(12) United States Patent
Jenkins, Jr.

(10) Patent No.: US 8,663,513 B2
(45) Date of Patent: Mar. 4, 2014

(54) FOAM EARPLUG EXTRUSION

(75) Inventor: John Allen Jenkins, Jr., San Diego, CA (US)

(73) Assignee: Honeywell International Inc., Morristown, NJ (US)

( * ) Notice: Subject to any disclaimer, the term of this patent is extended or adjusted under 35 U.S.C. 154(b) by 1462 days.

(21) Appl. No.: 11/890,841

(22) Filed: Aug. 7, 2007

(65) Prior Publication Data

US 2009/0039555 A1 Feb. 12, 2009

(51) Int. Cl.
*B29D 7/00* (2006.01)
(52) U.S. Cl.
USPC ........................................ 264/45.9; 264/45.1
(58) Field of Classification Search
USPC ....................................................... 264/45.9
See application file for complete search history.

(56) References Cited

U.S. PATENT DOCUMENTS

| | | | |
|---|---|---|---|
| 3,310,620 A | 3/1967 | Martelli et al. | |
| 3,981,663 A | 9/1976 | Lupke | |
| 4,449,910 A | 5/1984 | Leloux | |
| 4,504,206 A | 3/1985 | Lupke et al. | |
| 4,789,322 A | 12/1988 | Chan et al. | |
| 5,139,730 A | 8/1992 | Holso et al. | |
| 5,795,596 A | 8/1998 | Stanton et al. | |
| 5,935,500 A | 8/1999 | Stanton et al. | |
| 6,408,981 B1 | 6/2002 | Smith et al. | |
| 6,568,395 B2 | 5/2003 | Tiemens | |
| 6,659,103 B2 | 12/2003 | Tiemens | |
| 2003/0003181 A1 | 1/2003 | Hegler | |
| 2003/0029460 A1 | 2/2003 | Tiemens | |
| 2003/0075185 A1 | 4/2003 | Ulbrich | |
| 2004/0060567 A1 | 4/2004 | Ligon, Sr. et al. | |
| 2005/0056288 A1 | 3/2005 | Schreiber | |
| 2005/0109349 A1 | 5/2005 | Ligon, Sr. et al. | |

*Primary Examiner* — Christina Johnson
(74) *Attorney, Agent, or Firm* — Conley Rose, P.C.; Kristin Jordan Harkins

(57) ABSTRACT

Foam earplugs (90) are produced by extruding foamable material through a nozzle (12) having a throat (30) where the nozzle diameter is smallest, to produce an extrusion (34) that expands in diameter along an expansion zone (D) as the extrusion moves forward. Applicant moves dies (70, 72) against opposite sides of the extrusion and then moves the dies forward with the moving extrusion while the foam solidifies into earplugs. The earplugs to be formed have sealing portions that seal to a person's ear canal, of a maximum diameter G of about 0.4 inch, and the nozzle throat has a diameter B no more than 0.1 inch to provide a long expansion zone so the dies can begin to mold the extrusion while the extrusion is still expanding in diameter.

3 Claims, 4 Drawing Sheets

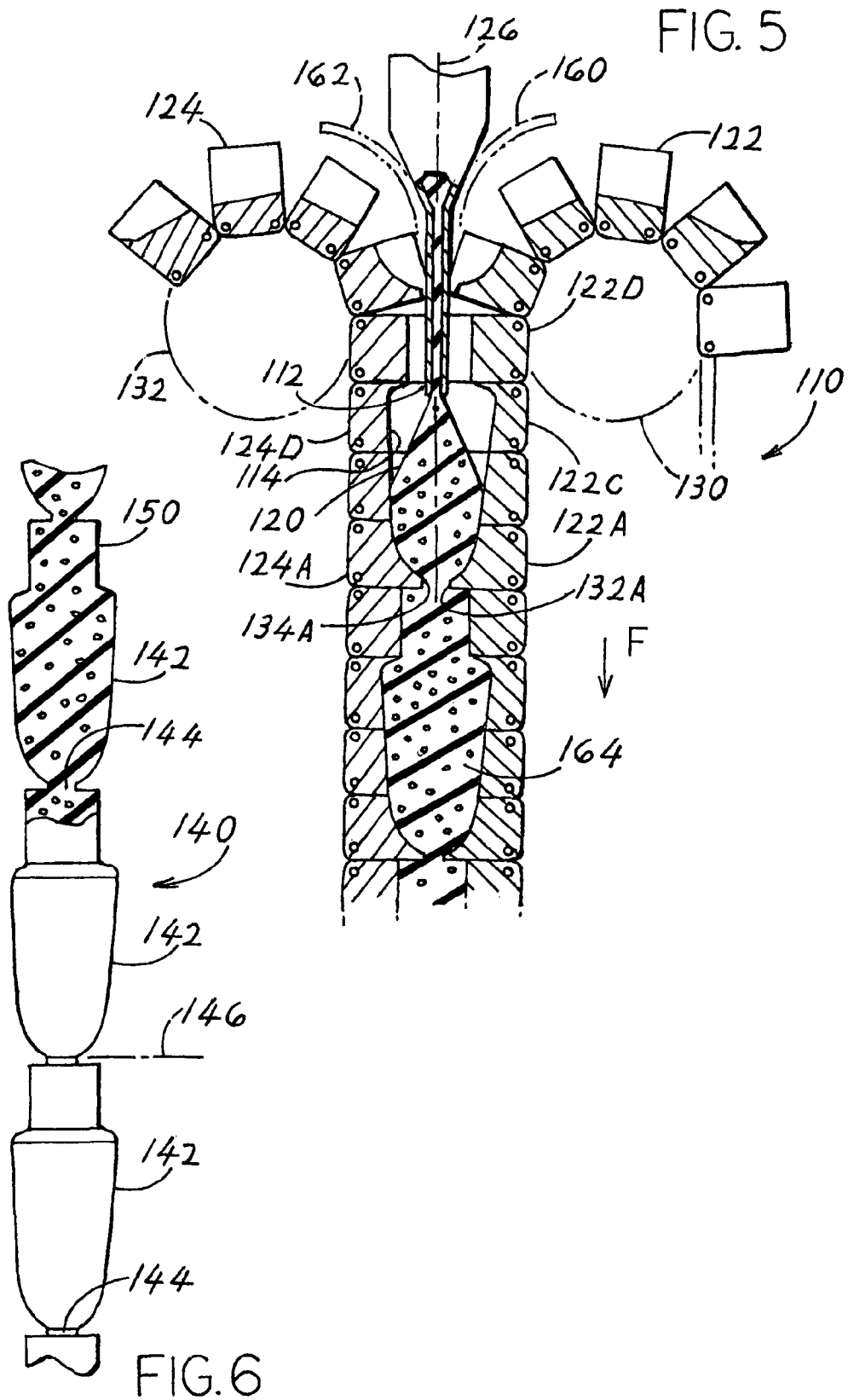

FOAM EARPLUG EXTRUSION

BACKGROUND OF THE INVENTION

Foam earplugs can be produced by extruding a foamable material through a nozzle and shaping the resulting foam extrusion. As the extrusion moves forward away from the nozzle, the extrusion expands for a short distance forward of the nozzle and begins to solidify. The extrusion can be shaped into earplugs in a number of ways. US patent publication 2004/0060567 describes one way of shaping, by moving dies against opposite sides of the extrusion and then moving the dies forwardly with the moving extrusion.

The extrusion can be most easily shaped using dies that form molds, by molding the extrusion while the foam is still expanding and while it has not solidified. However, it usually requires a distance along the extrusion to move the dies against the opposite sides of the extrusion and the extrusion usually has begun or finished solidifying by then. Systems and methods that allow the dies to mold the foam material while the extrusion is still expanding or soon after expansion has stopped, would be of value.

SUMMARY OF THE INVENTION

In accordance with one embodiment of the invention, a system and method are provided for molding earplugs from an expanding foam extrusion that moves forward from a nozzle, which facilitates molding of the extrusion while it is expanding or soon thereafter. The nozzle has a throat of a small diameter no more than one-fourth the diameter of the earplug sealing portion that enters the ear canal and seals to it, to extend the expansion zone along which the extrusion expands. This allows dies that mold the extrusion into earplugs, to move against the still-expanding extrusion. Opposite dies move together at a location spaced a distance from the nozzle throat that is no more than twice the earplug sealing diameter.

The dies that mold the earplug include first and second groups of dies at opposite sides of the extrusion. The dies are moved closely behind one another, and preferably with the rear end of one die against the front end of the subsequent die, to minimize wasting of extrusion material and removal of flashing. At least two short dies located in tandem, lie at each side of the extrusion portion that will form a single earplug, to facilitate moving the dies against the extrusion in or near the expansion zone.

The novel features of the invention are set forth with particularity in the appended claims. The invention will be best understood from the following description when read in conjunction with the accompanying drawings.

BRIEF DESCRIPTION OF THE DRAWINGS

FIG. 5 is a sectional view of an earplug extrusion system of still another embodiment of the invention, wherein the nozzle extends forward into a location where opposite dies are close together.

FIG. 6 is a side view of a string of earplug constructed using the system of FIG. 5.

DETAILED DESCRIPTION OF THE INVENTION

Figure 1:
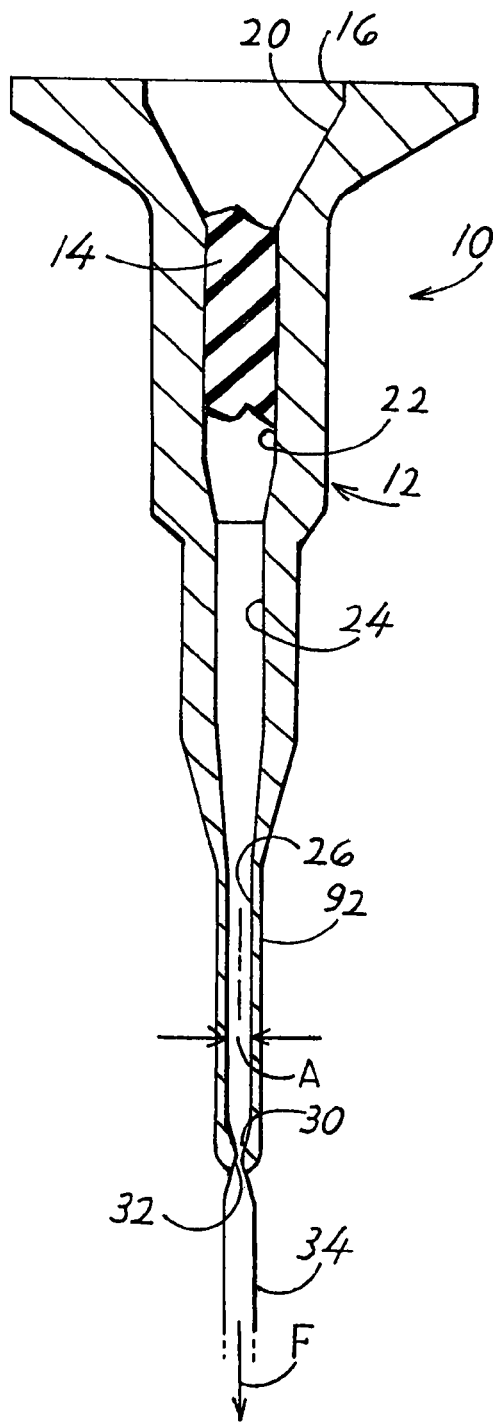
FIG. 1 is a sectional view of a nozzle of a system of the invention.
Figure 2:
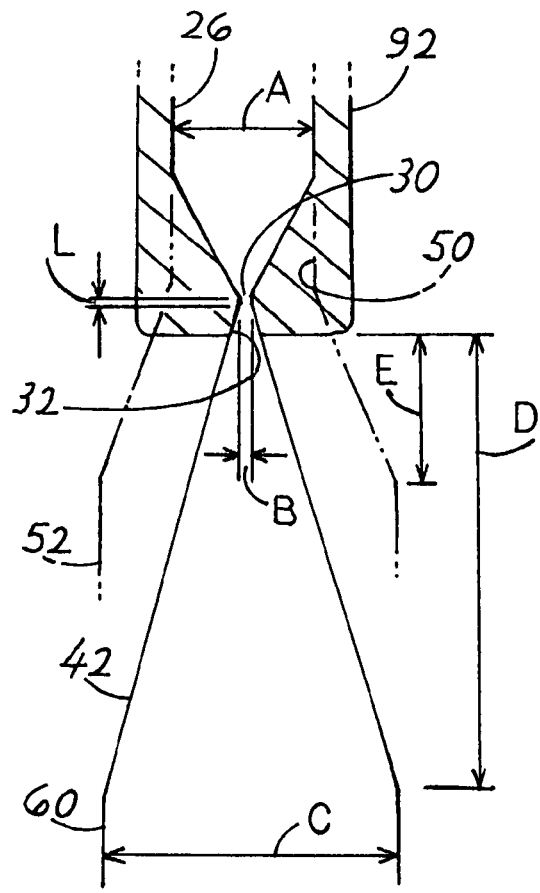
FIG. 2 is an enlarged view of a portion of the nozzle of FIG. 1.

FIGS. 1 and 2 show part of an extrusion system 10 of the invention which is used to form a large number of elastomeric slow recovery foam earplugs. Such earplugs can be rolled to a small diameter, inserted into the ear canal, and held there for perhaps a half minute while the earplug expands to seal to the ear canal. The extrusion system includes a nozzle 12 that extrudes a liquid foamable material 14 such as a foamable polytetrethylene. The foamable material is fed under pressure into the input end 16 of a through passage 20 of the nozzle. The liquid foamable material moves through passage portions 22, 24, 26 of progressively smaller diameters until it finally moves through a passage portion, or throat 30 of smallest diameter. The liquid foamable material then passes through a short expansion passage portion 32 that helps direct the foam extrusion 34. While in the passage upstream of the throat, the foamable material is under pressure and does not foam. However, once the liquid foamable material exits the throat 30, the material foams and begins to expand as it passes through the short expansion passage portion 32 and moves forwardly F beyond the nozzle and begins to solidify.

Figure 3:
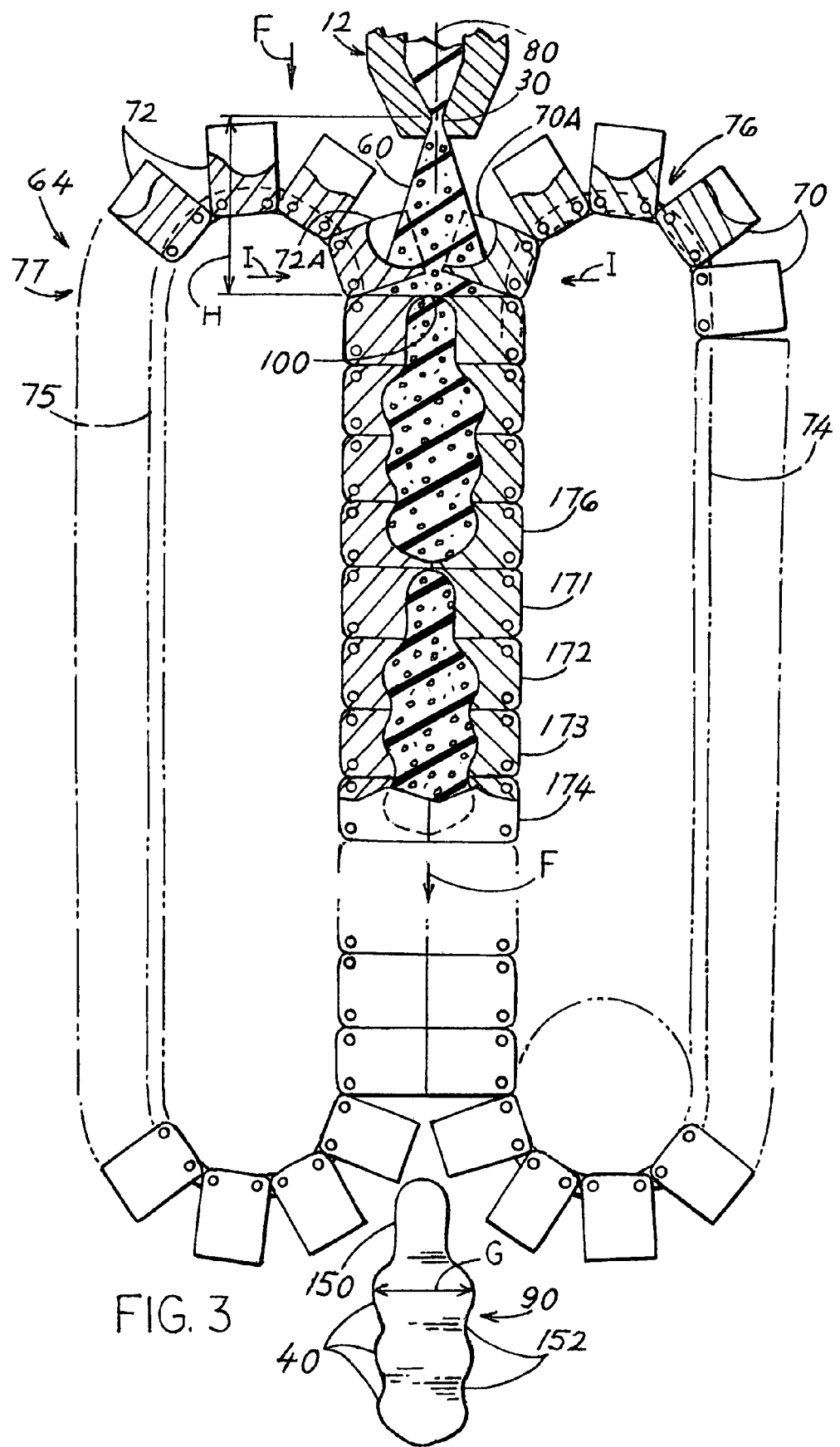
FIG. 3 is a sectional view of an earplug extrusion system of the invention that includes the nozzle of FIG. 1.

The earplugs, such as 90 in FIG. 3, each has a sealing portion 40 that enters the ear canal and seals to it, and that has a maximum diameter G (when not compressed) of about 0.4 inch (0.30 to 0.55 inch). The extrusion is formed so it expands to a diameter of about 0.5 inch. The nozzle 12 (FIG. 2) which is constructed to make such earplugs, has a passage portion 26 with an inside diameter A of 0.2 inch. The nozzle throat 30 has a diameter B (FIG. 2) of about 0.020 inch, which is about one-tenth the diameter A. Previously, in the making of earplugs by extrusion, applicant would use a nozzle with a smallest diameter portion of about 0.2 inch, and include sufficient gas and pressure so the extrusion expanded to a final extrusion 52 of a diameter of about 0.5 inch which is 2½ times its original diameter. Complete expansion of the extrusion occurred at a distance E such as 0.2 inch downstream of the nozzle tip, which is about 100% of the nozzle diameter A. However, applicant has found that full foaming expansion of the extrusion can be delayed to a longer distance downstream of the nozzle tip, by including the very small diameter throat 30.

The smallest diameter passage portion at throat 30, of 0.02 inch diameter produces an extrusion 60 of the desired size C (FIG. 2) by control of gas pressure. However, the expanding upstream extrusion portion 42 reaches its full diameter C at a distance D from the nozzle 12 that is significantly greater than the distance E for the prior extrusion 52 produced by the nozzle 50 of larger throat diameter A. This greater distance enables shaping of the extrusion to be accomplished more effectively.

FIG. 3 shows a shaping mechanism 64 for shaping the extrusion 60 produced by the small diameter nozzle throat 30. The extrusion is shaped by dies 70, 72 that move against opposite sides of the extrusion while also moving downstream or forward F along the direction of the extrusion movement out of the nozzle. Each of the dies is mounted on a chain 74, 75 that extends in loops and that form a die mover or transport. As the dies such as 70 move around the upper loop 76 they move radially inwardly towards the axis 80 of the extrusion while also moving parallel to the axis, and the dies also turn. When the die 70A digs into the extrusion, it thereafter turns by only a small angle of about 30° and then moves forward F without turning. It is desirable that the still-turning die 70A engage a location along the extrusion that is of minimum diameter and where the material is still foaming, so the extruded material is easily displaced by the die and so the material expands to fill any gap resulting from the die turning. By applicant forming the extrusion head as described above to produce an extrusion 60 that has a long expansion zone along which the extruded material foams, applicant is able to obtain a well formed earplug, which is shown at 90. Applicant notes that it is usually desirable to place the dies that are digging into the extrusion at 70A, 72A as close as possible to the nozzle opening, but other considerations such as the need for clearance, results in the die 70A moving into the extrusion a considerable distance downstream of the nozzle opening.

The inside of the nozzle of FIG. 2 has a throat 30 of small length L that is preferably no more than 0.2 inch. This minimizes friction of the material being extruded against the walls of the nozzle. The guide portion 32 can have a small length such as about the inside diameter B of the nozzle. The nozzle portion 92 upstream of the throat which has an inside diameter A, is provided with a long outside length primarily to provide room for the shaping apparatus of FIG. 3 to be attached to the nozzle.

The nozzle of FIG. 2 with an inside diameter B of 0.02 inch is constructed to create a foaming extrusion that expands to a diameter C of 0.5 inch that is 25 times the diameter of the narrowest part 30 of the nozzle. The narrowest part or throat 30 of the nozzle has a diameter which is preferably no more than 0.1 inch diameter, no more than one-fifth the final extrusion diameter, and no more than one-fourth the earplug maximum sealing portion diameter. The throat more preferably has a diameter no more than 0.05 inch (no more than one-tenth the final extrusion diameter). This provides a greater distance forward of the nozzle before the extruded material stops foaming. In FIG. 2, the expansion distance D (plus the length of the guide portion 32) for the nozzle 30 of 0.02 inch diameter B is about 0.6 inch, which is about three times the expansion distance E for a comparable extrusion 52 from the nozzle 50 of a diameter A of 0.2 inch.

In FIG. 3 the distance H between the nozzle throat 30 and the location 100 where the dies fully close is about 0.75 inch. The earplugs such as 90 have a maximum diameter of about 0.4 inch. This results in the die 70A stopping its turning when the extrusion has about fully foamed and about reached its full diameter.

Figure 4:
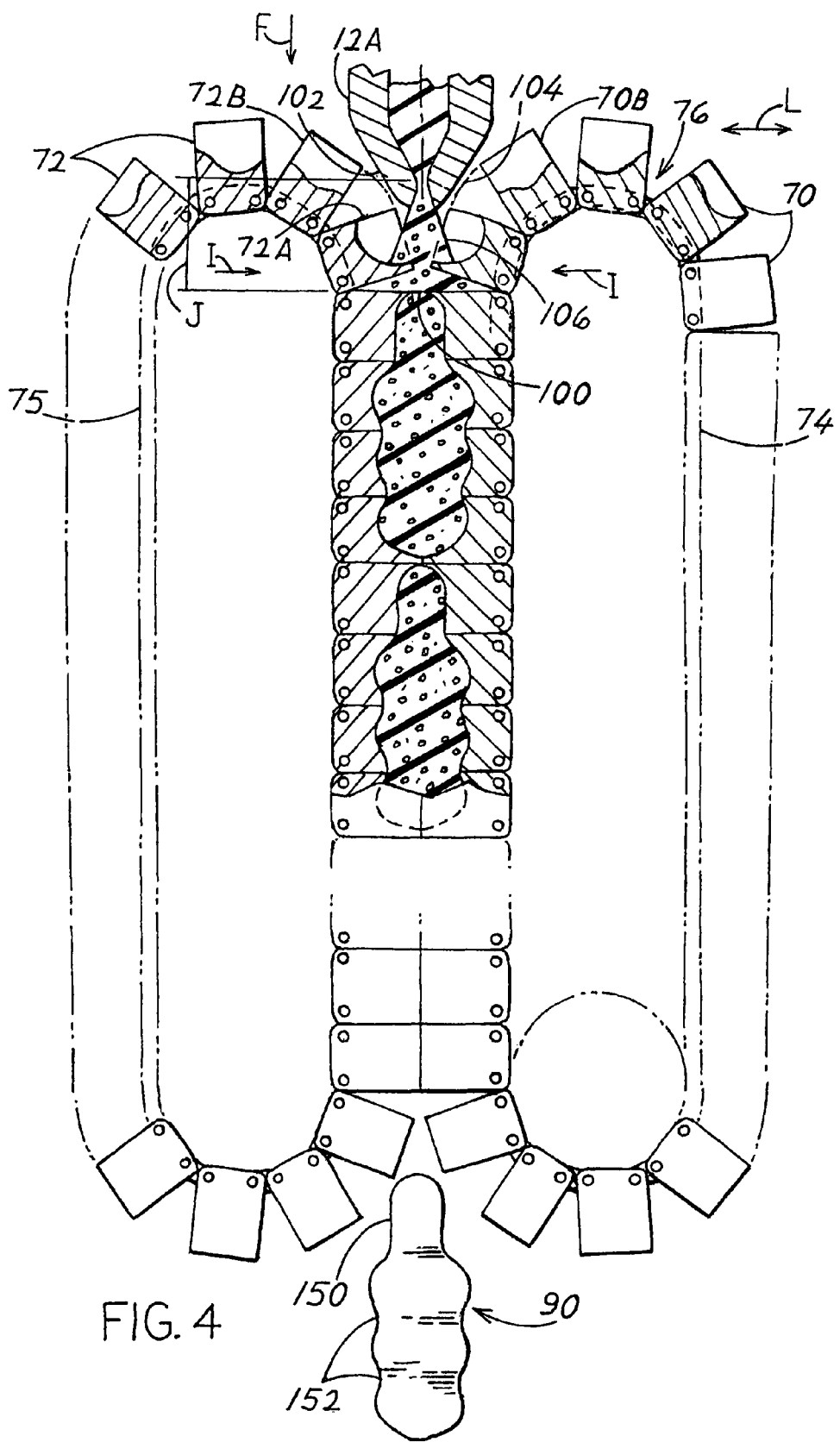
FIG. 4 is a sectional view of an earplug extrusion system of another embodiment of the invention, wherein the nozzle is shaped to enable the molding dies to move closer to the nozzle.

FIG. 4 shows a shaping system 76 where the nozzle 12A has been moved closer to the location 100 where the dies close. This is accomplished by shaping the die end 102 to avoid the paths 104 of the dies. A portion of the nozzle 12A lies laterally L between dies such as 70B and 72B which are the closest to next digging into the extrusion. In FIG. 4 the extrusion expansion distance to the closed dies at 100 has been reduced to a distance J which is only about 0.5 inch. As a result, the extrusion 106 is still foaming when being shaped by the dies, and is more likely to fill the cavities formed by the dies. The cavity resulting from a set of dies (e.g. 171-174 in FIG. 3 and the dies on the other side of the cavity), forms a majority of each earplug outside surface, and actually forms substantially the entire outside surface of each earplug.

FIG. 5 shows another system 110 wherein the nozzle end at 112 lies within a mold cavity 114. The extruded material 120 is extruded along an axis 126 into the mold cavity as the mold cavity is formed by dies 122, 124. The mold cavity is formed by dies that are moving around circles 130, 132 wherein the dies turn, and the dies then move forward F without turning. One pair of dies 122A, 124A or 122D, 124D forms an end of the cavity which has a smaller diameter than the rest of the cavity. In FIG. 5 the dies 122A, 124A form smallest diameter (relative to axis 130) cavity portions at 132A. This results in a string 140 of earplugs as shown in FIG. 6.

The string 140 of earplugs includes earplugs 142 that are joined by small diameter joints 144. Each joint can be cut, preferably at 146.

In the earplugs of FIGS. 3 and 4, the partially solidified foam is radially (toward its axis) compressed at selected locations such as at a handle 150. The process of FIG. 5 is suitable for forming earplugs of slow recovery material. The process of FIG. 5 can be used for earplugs of fast recovery foam if a stiffener can be provided. FIG. 5 indicates two stiffener half-tubes at 160, 162 of stiffer material than the extruded material 164. The half tubes are moved to lie along the axis of the earplug.

In the shaper mechanisms of FIGS. 3-5, each earplug is formed by a plurality of dies at each side of the extrusion. For example, FIG. 3 shows four dies 171-174 on one side of the extrusion portion that forms one earplug. The four dies at each side are used to enable the dies to move into the extrusion at a location close to the nozzle. A die (e.g. 171, in FIG. 3) at the rear end of an earplug, abuts or lies very close to a die such as 176 at the front of the next earplug, to minimize waste. It is possible to slide dies instead of turning them.

Thus, the invention provides an earplug extrusion system which includes a nozzle for producing a forwardly-moving extrusion that expands, and a shaping mechanism that shapes the extrusion into earplugs. The nozzle has a throat diameter that is less than one-fourth or one-fifth the diameter of the shaped earplug sealing portion to provide a greater extrusion expansion zone. A plurality of dies lies at each side (of two or more opposite sides) of each earplug so the dies can bite into the extrusion close to the nozzle. The dies preferably move in paths that extend on opposite sides of the nozzle. Other die arrangement can be used wherein the extrusion is molded.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for forming earplugs that are each of a predetermined length, by extruding a foamable material from a nozzle to produce a forwardly-moving extrusion that expands in diameter along an expansion zone, and by shaping the extrusion with earplug-molding cavities that define the shapes of said earplugs by moving dies that define said cavities against opposite sides of said extrusion and moving the dies parallel to the movement of the extrusion, wherein:

said step of moving dies includes moving dies into positions closely behind one another at each of said opposite sides of said extrusion to form said earplug-molding cavities between said dies wherein said earplug molding cavities are filled with material of said extrusion, said step of moving said dies closely behind one another includes leaving a space of no more than 10% of the length of each earplug between subsequent dies, wherein:

said earplugs each has a predetermined final maximum diameter of about 0.4 inch;

said step of extruding includes extruding said foamable material through a nozzle having a throat diameter of no more than 0.05 inch, whereby to provide a long extrusion expansion so the dies form said cavities while said foamable material is still expanding.

2. A method for forming foam earplugs that each has a sealing portion of a diameter of about 0.4 inch, by extruding a foamable material from a nozzle to produce a forward-moving extrusion that is expanding in diameter along an expansion zone that extends forward from said nozzle, and by shaping the extrusion, wherein:

said step of shaping the extrusion includes moving dies against opposite sides of the extrusion to form mold cavities between the dies, wherein said mold cavities shape a majority the outside of each earplug, including moving said dies against said extrusion at a location where the extrusion is still expanding, so material of the extrusion can expand to completely fill the mold cavities formed by said dies, wherein:

said step of extruding includes extruding said foamable material through a nozzle throat which has an inside diameter of no more than 0.05 inch, whereby to provide a long expansion zone and therefore room for the dies to move into said expansion zone.

3. A method for forming foam earplugs that each has a sealing portion of a diameter of about 0.4 inch, by extruding a foamable material from a nozzle to produce a forward-moving extrusion that is expanding in diameter along an expansion zone that extends forward from said nozzle, and by shaping the extrusion, wherein:

said step of shaping the extrusion includes moving dies against opposite sides of the extrusion to form mold cavities between the dies, wherein said mold cavities shape a majority the outside of each earplug, including moving said dies against said extrusion at a location where the extrusion is still expanding, so material of the extrusion can expand to completely fill the mold cavities formed by said dies, wherein:

said step of extruding comprises extruding said foamable material through a nozzle throat of no more than 0.02 inch diameter.

* * * * *